United States Patent [19]

Inlow et al.

[11] Patent Number: 5,024,947

[45] Date of Patent: Jun. 18, 1991

[54] SERUM FREE MEDIA FOR THE GROWTH ON INSECT CELLS AND EXPRESSION OF PRODUCTS THEREBY

[75] Inventors: Duane Inlow; Brian Maiorella, both of Oakland, Calif.

[73] Assignee: Cetus Corporation, Emeryville, Calif.

[21] Appl. No.: 77,303

[22] Filed: Jul. 24, 1987

[51] Int. Cl.$^5$ .............................................. C12N 5/00
[52] U.S. Cl. ........................... 435/240.31; 435/240.1; 435/240.2; 435/240.3; 435/70.1
[58] Field of Search .............. 435/240.2, 240.3, 240.31

[56] References Cited

U.S. PATENT DOCUMENTS

| | | |
|---|---|---|
| 30,985 | 6/1982 | Cartaya . |
| 4,485,029 | 11/1984 | Kato et al. . |
| 4,752,585 | 6/1988 | Koths et al. ........................ 435/256 |

FOREIGN PATENT DOCUMENTS

| | | |
|---|---|---|
| 0055835 | 7/1982 | European Pat. Off. . |
| 3216163 | 11/1985 | Fed. Rep. of Germany . |
| 58-31989 | 2/1983 | Japan . |

OTHER PUBLICATIONS

The Merck Index, 9th edition, Merck & Co., Inc. (1976), pp. 7349, 2435.
Smith et al.(b), Proc. Natl. Acad. Sci. 82:8404-8408 (1985).
Brooks et al., in "Verteb. Syst. in Vitro", eds Kinstak et al., Elsevier, Amsterdam, Netherlands (1980), pp. 67-77.
Mitsuhashi, Adv. in Cell Culture 2:133,156-7, 182-3 (1982).
Kawasaki et al., Science, 230:291-296 (1985).
Keay, Methods Cell Biol., 20:169,194-195 (1978).
Miltenburger, in "Horm: Def. Media", eds. Fischer et al., Springer: Berlin, FRG (1983), pp. 31-43.
Jeang et al., J. Virology, 61:708-713 (1987).
Smith et al. (1), Mol. Cell. Biol., 3:2156-2165 (1983).
Mizrahi, J. Clinical Microbiol., 2(1):11-13 (1975).
Ryan, P. A. et al., 1987, Exp. Cell Res., 172:318.
Bettger, W. J., 1981, PNAS(USA), 78:5588-5592.
Iscove, N. N., 1984, Methods for Serum-Free Culture of Neuronal and Lymphoid Cells, 4:169-185.
Mizrahi, A., 1984, Devel. Biol. Standard, 55:93-102.
Derwent Publication (Abstract Only), No. 4,476,618.
Kirk-Othmer Encyclopedia of Chemical Technology (John Wiley & Sons, Inc., N.Y.).
Kilburn, et al., 1968, Biotech & Bioengin., X:801-814.
Yamane, et al., 1981, Proc. Japan Acad., 57B(10):385-389.

*Primary Examiner*—Elizabeth C. Weimar
*Assistant Examiner*—Jasemine C. Chambers
*Attorney, Agent, or Firm*—Leona L. Lauder; Wean Khing Wong

[57] ABSTRACT

Serum-free media which support the growth of insect cells and the production thereby of recombinant proteins and viral products are herein disclosed. The serum free media can support insect cell growth at large scale under agitated and/or sparged, preferably well-aerated conditions.

The serum free medium disclosed support insect cell growth to cell densities comparable to serum-containing culture and the production of viral and recombinant products to levels equivalent to those found in serum containing culture.

14 Claims, 2 Drawing Sheets

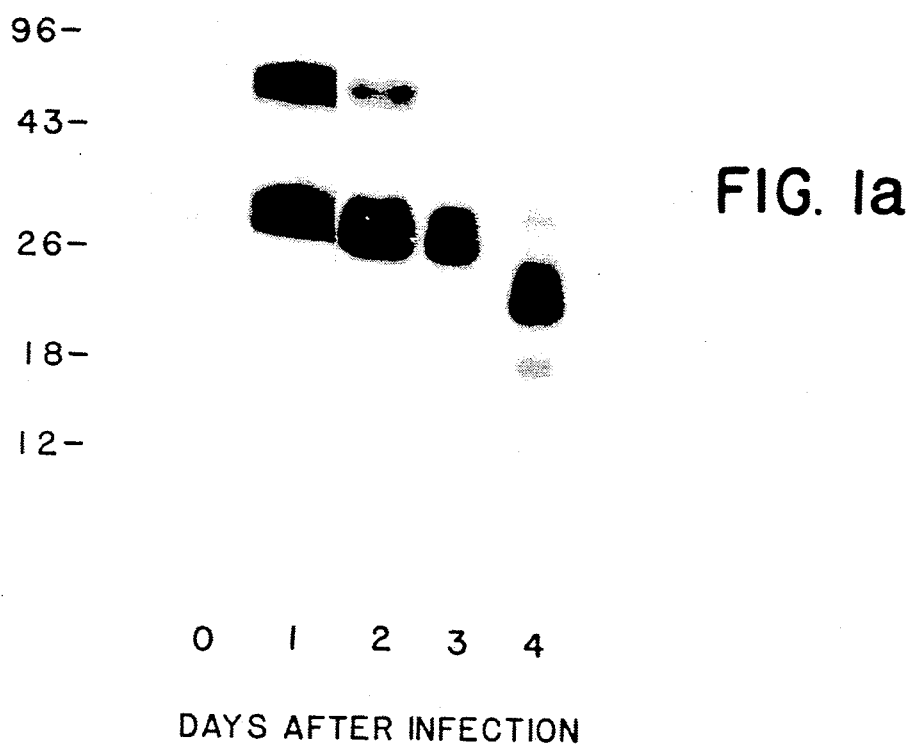

SERUM FREE MEDIA FOR THE GROWTH ON INSECT CELLS AND EXPRESSION OF PRODUCTS THEREBY

FIELD OF THE INVENTION

This invention is in the field of fermentation and insect cell culture. More particularly, the invention concerns improved media for the cultivation and reproduction of insect cells. Further, this invention concerns serum free media which support the large scale growth of insect cells. Still further, this invention concerns the expression at high levels of recombinant or viral products by insect cells grown in said serum free media that are infected respectively either by a recombinant baculovirus or by a wild-type virus.

BACKGROUND

Insect cells have been successfully used to replicate baculoviruses to promote expression of foreign genes carried by baculoviruses. [Smith et al., PNAS (U.S.A.), 82:8404–8408 (December, 1985) wherein *Spodoptera frugiperda* cells infected with recombinant *Autographa californica* nuclear polyhedrosis viruses (AcNPV) carrying cDNA coding for human IL-2 are reported to produce high levels of IL-2; see also, Smith et al., European Patent Application Publication No. 127,839 (published Dec. 12, 1984), wherein methods for producing recombinant baculoviruses capable of expressing selected genes in host insect cells are disclosed; and Jeang et al., *J. Virol.*, 61 (3):708–713 (March 1987), wherein the production of functional human T-cell leukemia virus type I (HTLV-I) p40$^x$ protein by *S. frugiperda* (Sf9) cells infected with a recombinant AcNPV virus is reported.]

Insect cells have been cultured for the production of insect viruses as biological insecticides. [Vaughn et al., *In Vitro*, 13:213–217 (1977); Lynn et al., *J. Invert. Pathol.*, 32:1–5 (1978)]. Such viruses include, for example, baculoviruses and non-baculoviruses such as infectious flacheriae virus (IFV) and cytoplasmic polyhedrosis virus (CPV). Exemplary are certain baculoviruses, for example, nucleopolyhedrosis viruses (NPV) and granulosis viruses (GV), which are highly virulent for pest insects; some of the most promising have been commercially developed as biological pesticides pathogenic for agriculturally important insects. [Burges (ed.), *Microbial Control of Pests and Plant Diseases* 1970–1980 (London, 1981); Miltenburger et al., *Bioinsecticides II: Baculoviridae. Adv. Biotechnol. Processes*, 3:291 (1984); for a discussion of such NPV and GV products as biological pesticides, see Shieh et al., "Production and Efficiency of Baculoviruses," *Biotechnology and Bioengineering Vol. XXII*, 1357 (1980); see also Huber, "Use of Baculoviruses in Pest Management Programs," In Granados et al., (eds.), *The Biology of Baculoviruses:* Vol. II Practical Applications for Insect Control, pp. 181–202 (1986).]

Baculoviruses are very stable and are able to persist for longer times in the environment than other animal viruses. This unusual biological stability is the result of a unique association of the infectious virus particles and a viral occlusion which is a crystalline assembly of a viral encoded structural protein called polyhedrin. Late in viral replication, baculovirus particles become embedded in a protein occlusion composed of the polyhedrin protein. Insects acquire a baculovirus disease by ingesting these occluded virus (OV) contaminating their food supply. The polyhedrin matrix protects the virus particles outside of the insect and also during their passage through the foregut of the insect. In the insect midgut, the alkaline pH activates the dissolution of the polyhedrin crystalline matrix resulting in the release of many viruses. The virus becomes absorbed by the midgut epithelial cells initiating the infection process. There is a second infectious form of nuclear polyhedrosis viruses (NPVs), known as the extracellular or nonoccluded virus (NOV) form, which is generated by the budding of viral nucleocapsids through the plasma membrane of the infected cells. NOVs are responsible for spreading the secondary infection via the hemolymph of the insect.

Traditionally, production of baculoviruses was achieved using insect larvae; however, large sale production by such means is not attractive. Insect cell culture is much more practical. [Vaughn, *Adv. Cell. Cult.*, 1:281–295 (1981); Stockton et al., In Burges (ed.), supra, at 313–328.] Batchwise and semicontinuous production of *Spodoptera frugiperda* and *Trichoplusia ni* cells that allow the replication of *Autographa californica* nuclear polyhedrosis virus have been reported. [Vaughn, *J. Invert. Path.*, 28:233–237 (1976); Hink, In Kurstak (ed.), *Microbial Viral Pesticides* at 493–506 (1982).]

To obtain the maximum yield of insect cells in culture with minimum population doubling time, the cells must be provided with ideal nutritional, biological, and biophysical requirements for growth. One of the most important variables is the composition of the insect cell culture media. The basis of a commonly employed medium f 15 for lepidopteran cells was a medium developed by Wyatt, *J. Gen. Physiol.*, 39:841 (1956) and modified by Grace, *Nature* (London), 195:788 (1962). That medium > resembles hemolymph and consists mainly of chemically pure amino acids, vitamins, organic acids and inorganic salts, and originally was supplemented with insect hemolymph. Later the hemolymph from this formulation was replaced by fetal bovine serum, bovine serum albumin, and whole-egg ultrafiltrate.

[Weiss et al., Chapter 3, page 68, In Granados et al. (eds), *The Biology of Baculoviruses* (Vol. II) 1986; citations omitted.]

The cultivation of insect cells in vitro at large scale, infecting the cells with either recombinant or non-recombinant viruses, and work-up of the recombinant product or the virus material depends on the availability of a suitable culture medium. As indicated above, conventional culture media contain, in addition to inorganic salts, vitamins, amino acids, sugars, and a number of other organic compounds important for cell physiology, about 2–25% by weight per volume of animal serum and/or animal serum albumin. Animal serum is a limiting factor due to its high price and relatively scarce availability, and further, because of the complications it creates for product purification. Production of insect cells on a scale required for either the industrial manufacture of insect pathogenic viruses or of recombinant products necessitates the replacement of animal serum by a cheaper component available in sufficient quantities.

There have been a number of studies done to develop serum-free media for the cultivation of insect cells, many of which are in the context of producing NPV and GV as biological pesticides and which include the following: Goodwin et al., in Kurstak et al. (eds.) *Inver-* tebrate *Systems In Vitro*, Chapter 45:493–509 (1980); Goodwin, *In Vitro*, 12:303–304 (1976); Hink et al., *In Vitro*, 13:177 (1977); Roder, U.S. Pat. No. 4,454,227; Weiss et al., *In Vitro*, 20:271 (1984); Gardiner et al., *J. Invert. Path.*, 25:363–370 (1970); Wilkie et al., *Develop. Biol. Standard.*, 46:29–37 (1980); and Vail et al., *J. Invert. Path.*, 28:263–267 (1976).

Table 1 lists a number of the media wherein serum was replaced by protein hydrolyzates and crude and defined lipids. Such serum-free media were reported to support the production of baculovirus in insect (Lepidopteran) cells although some of the media did not produce viable occluded virus.

TABLE 1

| Lepidopteran Serum-Free Culture | | |
|---|---|---|
| Report | Cell Line | Medium |
| Hink et al. In Vitro, 13:177 (1977) | *Trichoplusia ni* | Defined medium + Bactotryptose |
| Goodwin et al., In Vitro, 12:303 (1976) | *Porthetria dispar* | Defined medium + liver digest, peptic peptone, yeast extract, Lactalbumin Hydrolysate |
| Roder, Naturwissenschaften, 69:92 (1982) | *Spodoptera frugiperda* | Defined medium + peptones, egg yolk |
| Weiss et al., In Vitro, 20:271 (1984) | *Heliothis zea* | RIL-2B medium + sterols, fatty acids |
| Goodwin et al., Invert. Systems, Chap 45:493 (1980) | *Lymantria dispar* | Defined medium + peptones, glutamine, glycerol, α-glycerophosphate, oleate, Tween 80, cholesterol, α-Tocopherol |

In regard to such serum free media, Weiss et al. points out in *The Biology of Baculoviruses*, (CRC Press 1986) supra, at page 68 that:

Research findings on the role and utilization of amino acids, minerals, hormones, mitogens, carbohydrates, organic acids, fatty acids, sugars, lipids, and monovalent and divalent cations in cultured insect cells have led to some experimental application of serum-free media for insect cells. However, to date these serum-free media are not completely satisfactory for viral replication, which may be attributed to the absence of undefined proteins normally in serum supplements. [Citations omitted.]

In the context of culturing insect cells for the production of recombinant proteins via a baculovirus expression vector system (BEVS), Miller et al. [In: Setlow et al. (eds.), *Genetic Engineering Principles and Methods* (Vol 8): "An Insect Baculovirus Host-Vector System for High-Level Expression of Foreign Genes," pp. 277–298 (1986)] states at page 291: "Typically 10% fetal calf serum is present throughout cell and viral growth. The protein contributed by the serum can be a problem for purification and perhaps expression if it contains certain antagonistic activities. While the literature contains reports of insect cells growing in serum-free media, such media do not readily support viral growth." Miller et al. then notes that U.S. Pat. No. 4,454,227 to Roder wherein an egg yolk emulsion is used as a serum replacement is an "interesting exception" but that it "is not clear that it eases purification problems. As a short term solution, we have observed that, once infected in 10% serum-containing media, cells can be transferred to a serum-free media and expression will occur largely unabated." However, such a transfer from serum-containing medium to a serum free medium, as suggested by Miller et al., is not a practical solution for large scale industrial production.

Summers et al. in "A Manual of Methods for Baculovirus Vectors and Insect Cell Culture Procedures" Texas Agricultural Experiment Bulletin No. 1555 (Texas A & M University; May 1987) recommends, at pages 32–33, the use of "Grace's Antheraea medium (a relatively simple mixture of salts, carbohydrates and amino acids) . . . used for short term incubations of cells (rinsing monolayers, seeding cells, transfection, etc.)" and "TNM-FH, a more complete medium suitable for routine growth of cells in monolayer or suspension, . . . prepared from Grace's by the addition of 3.3 g/liter Yeastolate and 3.3 g/liter Lactalbumin Hydrolysate (both available from Difco)." Summers et al. goes on to state at page 33 that for "complete growth medium, add 10% fetal bovine serum (sterile, heat inactivated", and under the Methods section at pages 9 and 11, Summers et al. directs that "TNM-FH media+10% FBS+antibiotics" be used. At page 10, Summers et al. states: "It is desirable to seed cells in serum-free medium to promote rapid and firm attachment for plaque assays, infections, etc. However, cells may begin to show signs of stress if they are left without serum for more than 2 hours."

Most culture media for the growth of insect cells contain peptones and serum and are conventionally used to grow insect cells under poorly aerated conditions which restrict the cells' growth and expression of recombinant proteins and viable viral particles. Although serum-free media have been developed that support insect cell growth, none of such media have been shown to support production of levels of recombinant proteins from insect cells grown in such serum-free media and infected with a recombinant baculovirus, comparable to levels achieved from insect cells so infected and grown in approximately 10% serum-containing media. Further, as indicated above, none have been shown to support viral replication in insect cells satisfactorily.

Attempts to include lipid nutrients in insect culture media have often resulted in the presence of large insoluble lipid particles not easily available to cells. This invention solves that problem.

The research described herein indicates that some of the peptones and other ingredients included in published insect culture media, both serum and non-serum containing, are growth inhibitory or unnecessary. Further, the research indicates that high molecular weight components of the peptone fractions may interfere with the purification of the recombinant or viral products produced by the cultured insect cells; this invention provides a means to remove such components.

Further, of great value to the art would be a single serum-free, low or no protein medium for the growth of insect cells and production of recombinant proteins or viral products thereby respectively either via a baculovirus expression vector system (BEVS) or by infection with a wild-type virus. On a small scale, insect cells can be grown in a serum-containing relatively high protein medium, and can then be separated from such growth medium and resuspended in a serum-free production medium for infection and expression of products. Such separation and resuspension processes are not desirable for large scale culture because of the complexity of the equipment and operations required for such procedures. There is a need in the art for a single serum-free and low or no protein growth and production medium which would simplify fermentation operations, reduce the cost of large scale insect cell culture, and aid in the purification of the recombinant and viral products. This invention meets that need.

A reason that poorly aerated conditions have been conventionally used in insect cell culture is because of "the fragility of insect cells". [Weiss et al., *The Biology of Baculoviruses*, Vol. II (Chapter 3) at page 80 (CRC Press 1986); Weiss et al., *In Vitro*, 16:222 (1980).] "Two problems appear to have delayed the full utilization of suspension systems for the large volume culture of insect cells: the fragility of insect cells, and second, the high oxygen demand, particularly for virus-infected cells." [Weiss et al., CRC Press, supra, p. 80; citations omitted.] Tramper et al., *Enzyme Microb. Technol.*, 8:33–36 (January 1986) notes at p. 33: "A major problem encountered in scaling up [insect] cell culture systems is the shear sensitivity of these cells due to their size (20 μm range) and lack of cell wall. The shear sensitivity may hamper the supply of sufficient oxygen in a conventional manner (e.g., by sparging)." Tramper et al. further states at pages 35–36:

The mechanical strength of insect cells in culture is small . . . This has definite consequences for the scale up of insect cell cultures. Larger volumes of insect cell cultures require more efficient oxygen transfer to the solution than can be achieved by flushing air/oxygen over the liquid surface. However, dispersion of gas by means of stirring and sparging air through the cell suspension to provide sufficient oxygen probably results in a larger decay rate than growth rate of the cells.

The instant invention meets the need of providing a medium in which insect cells can grow not only under the poorly aerated conditions of conventional culture, but in well-aerated conditions wherein insect cells can grow to high cell density with high viability and produce levels of recombinant products, when infected with recombinant baculoviruses, or of other viral products, when infected with wild-type viruses, comparable to levels achieved in serum-containing media.

SUMMARY OF THE INVENTION

The present invention provides for serum-free low or preferably no protein media for the large scale growth of insect cells to high cell density with high viability. The media of this invention support insect cell growth to densities equivalent to those found in serum-containing media that have much higher protein content. Further, when insect cells are grown in the media of this invention, the expression of recombinant products thereby and the production of other viral products, such as, NPV and GV, are equivalent to the expression and production of insect cells grown in serum-containing media.

Further, this invention provides for serum-free media that support both the growth of insect cells as well as the production of recombinant proteins and other viral products, and is further compatible with the purification of such recombinant proteins and viral products.

Further, another aspect of this invention is an optional method of removing by ultrafiltration, high molecular weight components, residual proteases and endotoxins from the peptone fraction that had not been removed during its manufacture and which might interfere with purification of viral and recombinant products of the insect cells. Therefore, another aspect of this invention is serum-free media for insect cell culture which are substantially free of high molecular weight components, residual proteases and endotoxins.

Also, this invention provides a lipid component in the form of a microemulsion in the serum-free media. Such lipid component comprises a lipid/organic solvent solution containing a small amount of an emulsifier, or of a combination of emulsifiers. Preferred emulsifiers include the combination of a phospholipid, such as, lecithin, or more preferably a non-toxic, non-ionic polymeric detergent, such as, polysorbate 80, and a second emulsifier, preferably, a non-ionic polymeric detergent, more preferably, a Pluronic polyol, still more preferably Pluronic F68 or F88.

Further, the serum-free media of this invention optionally comprise a non-toxic protective agent that prevents cell damage and death caused by shear stress in agitated and/or sparged cultures. Preferred non-toxic protective agents of this invention are non-toxic water soluble polymers, more preferably non-toxic, non-ionic polymeric detergents, Pluronic polyols, such as Pluronic F68 or Pluronic F88, still more preferably Pluronic F68.

FIGURE DESCRIPTION

FIG. 1 illustrates the time course for the production of rCSF-1 by Sf9 insect cells infected with recombinant baculovirus AcM6. The upper panel indicates the concentration of rCSF-1 as determined by RIA at 0–4 days post-infection. The middle panel indicates the viability of the insect cells as determined by counting cells using Trypan blue exclusion method over the same time period. The lower panel is a Western blot analysis of rCSF-1 produced.

DETAILED DESCRIPTION

Figure 1B:
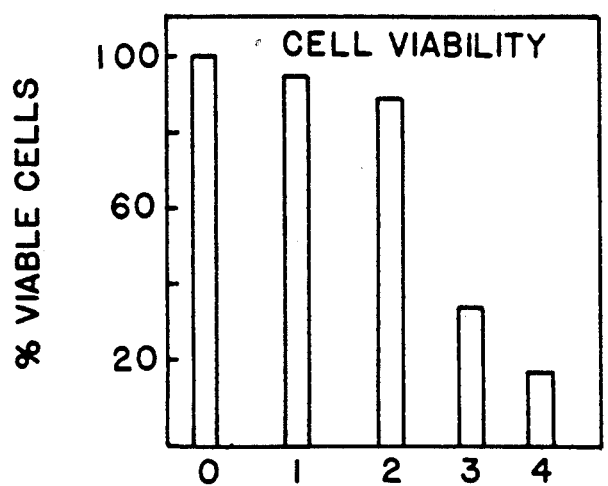

The serum-free, low protein or preferably no protein media of this invention are designed for the growth of insect cells at large scale. The media of this invention provide a good nutritional environment for the growth of insect cells in agitated and/or sparged, and preferably well-aerated conditions. Insect cells have a "high oxygen demand, particularly for virus-infected cells." [Weiss et al., CRC Press, supra, p. 80.] Therefore, media of this invention have also been designed to enhance cell growth and production of viral and recombinant products from insect cells and to protect the cells from damage or death under well-aerated conditions which are more physically demanding than static cultures or other conventional cultures which are less well-aerated.

"Well-aerated" herein refers to non-oxygen limited conditions as those created by agitation, for example, in spinner or roller bottles and stirred or shake flasks, or by sparging, for example, in airlift fermentors. Co-pending, commonly owned U.S. Ser. No. 07/077,181 entitled "Airlift Insect Cell Culture" which is being concurrently filed with the instant application, discloses successful culturing of insect cells in airlift fermentors and is herein incorporated by reference.

The term "protein" is herein defined to exclude the term "peptones." The serum-free media of this invention preferably contain very low concentrations of protein, that is, less than about 1000 µg/ml, more preferably less than about 50 µg/ml, and still more preferably less than about 5 µg/ml, and even more preferably no protein.

The term "peptone" is defined herein as a mixture of cleavage products produced by the partial hydrolysis of a native protein either by an acid or an enzyme. Peptones used in the serum-free media of this invention are preferably of a molecular weight less than about 15,000, and more preferably of a molecular weight less than about 10,000.

In one aspect of this invention, the serum-free media of this invention include:
(a) a basal medium;
(b) a lipid component; and
(c) a peptone component.

A "basal medium" is herein defined as a nutrient mixture of inorganic salts, sugars, amino acids, optionally also containing vitamins, organic acids and/or buffers. Basal media together with supplements provide the nutrients necessary to support cell life, growth and reproduction. The preferred basal media used as the starting point for the preparation of the serum free media of the present invention contain neither serum, nor proteins, nor preferably any peptones. The choice of basal medium for the preparation of the media of this invention is not critical. The basal medium can also be considered optional in the sense that appropriate peptone and lipid components can be selected which provide such necessary nutrients as amino acids and vitamins required to support cell life, growth and reproduction.

There are a wide variety of commercially available basal media that can be used in the media of this invention. Such commercially available basal medium include, for example, TC10 without tryptose broth [commercially available from Microbiological Associates; see Gardiner et al., *J. Invert. Pathol.*, 25:363 (1975)], Grace's Antheraea medium [Vaughn et al., TCA Manual, 3(1) (1976); Yunker et al., *Science*, 155:1565–1566 (1967)], Medium M20 of Mark's [Vaughn et al., *TCA Manual*, 3 (1) [1976]; Marks, In Kruse et al. (eds.), *Tissue Culture Methods and Applications*, pp. 153–156 (1973)], Goodwin's IPL-52 Medium [Goodwin, *In Vitro*, 11:369–378 (1975)], Goodwin's IPL Medium [Goodwin et al., In Kurstak et al. (eds.), *Invertebrate Systems In Vitro* (1980)], Goodwin's IPL-76 Peptone Medium [Goodwin et al., id.; Goodwin et al., *In Vitro*, 14:485–494 (1978)], Hink's TMH FH Medium (Revised) [Hink, *Nature* (London), 226:466–467 (1970)], Medium S-301 of Hansen [Hansen, In Maramorosch (ed.), *Invertebrate Tissue Culture Research Applications*, pp. 75–99 (1976); Vaughn et al., *TCA Manual*, 3(1) (1976)], and IPL-41 Medium [Weiss et al., *In Vitro*, 17 (6):495–502 (1981)], wherein IPL-41 is a preferred basal medium.

As indicated, IPL-41 is a preferred basal medium for the preparation of the media for this invention. IPL-41 basal medium is commercially available from a number of vendors and is described in Weiss et al., *In Vitro*, 17 (6):495–502 (June 1981) and in Weiss et al., *CRC Press*, supra, pp. 70–72 (1986). Table 1 of Weiss et al. (In Vitro) at page 496, and Table 3 of Weiss et al. *CRC Press*, at pages 71–72 outline all the components of IPL-41 and provide their proportions in mg/l; said tables are herein incorporated by reference. At page 497 of Weiss et al. (In Vitro), the preparation of the complete medium IPL-41 is described wherein tryptose phosphate broth (TPB) and fetal bovine serum (FBS) are added. The IPL-41 basal medium employed in preparing the serum-free media of this invention does not contain tryptose phosphate broth (TPB) or fetal bovine serum (FBS).

The serum-free media of this invention can further comprise a protective agent. Such a protective agent is a preferred component of the media of this invention, especially under well-aerated culture conditions. Therefore, the serum-free media of this invention include:
(a) a basal medium;
(b) a lipid component;
(c) a peptone component; and
(d) a protective agent.

A protective agent is necessary to prevent cell damage and death under well-aerated conditions as found in well agitated and sparged cultures. The protective agent prevents a disintegration/clumping phenomenon of insect cells grown in shake flasks and adherence of the cells to the vessel walls. Further, the protective agent reduces the amount of cellular debris in shake flask cultures indicating that cell lysis is reduced by the presence of the protectant. The protective agent further preferably acts as an anti-foaming agent preventing the loss of cells from the free suspension into a foam layer, and can act as a bubble surface tension reducing agent and/or as a cell surface stabilizing agent and/or as a viscosifying agent.

Protective agents are herein defined as non-toxic, water soluble compounds that functionally act to protect insect cells from damage and death in agitated and sparged insect cell culture. The protective agents of this invention are preferably non-toxic, water soluble polymers. A protective agent candidate can be selected by first confirming that it is not toxic to the insect cells to be cultured by methods known to those skilled in the art of insect cell culture, for example, by adding it to a suspension or monolayer of the insect cells of choice for cultivation and comparing the growth of the culture to a control. Then, the non-toxic protective agent candidates can be tested for protective ability by adding the candidate agent to an agitated or sparged culture of the insect cells of choice at small scale and observing viability and growth rate after an appropriate period and comparing the viability and growth rate of the cells of said culture to the viability and growth rate of the cells in a control culture.

The protective agents in the media of this invention are preferably cell surface stabilizing agents and/or viscosifying agents and/or bubble surface tension reducing agents. Examples of preferred protective agents are hydroxyethyl starch, methyl cellulose, carboxymethyl cellulose (as, sodium carboxymethyl cellulose), dextran sulfate, polyvinylpyrrolidone, ficoll, alginic acid, polypropyleneglycol, and non-toxic polymeric detergents.

Non-toxic polymeric detergents are preferred as protective agents in the media of this invention. Further preferred are nontoxic polymeric detergents which are non-ionic. Editions of McCutcheon's Emulsifiers & Detergents (published by the McCutcheon Division of MC Publishing Co., 175 Rock Road, Glenn Rock, N.J., U.S.A.) are examples of a source of finding non-toxic, non-ionic polymeric detergent candidates for protective agents for the media of this invention, which can be tested for non-toxicity and protective ability as indicated above. Preferred non-toxic, non-ionic polymeric detergents are block copolymers of propylene oxide and ethylene oxide (polyoxypropylene polyoxyethylene condensates), preferably Pluronic polyols, such as, Pluronic F68, F77, F88 and F108, preferably F68 and F88, more preferably F68. The Pluronic polyols are commercially available from BASF Wyandotte corp. (101 Cherry Hill road, P.O. Box 181, Parsippany, N.J. 07054, U.S.A.).

The protective agent is preferably present in the media of this invention at a concentration which is most effective in protecting the insect cells from damage, but which concentration is non-inhibitory to cell growth and reproduction. The Pluronic polyol polymeric protectants are present in the media of this invention preferably at a concentration (weight-volume) of from about 0.01% to about 1%, more preferably from about 0.05% to about 0.5%, and most preferably about 0.1%.

It is further preferred that the protective agent, preferably a polymeric protectant, also act as an emulsifier of the lipid component of the media of this invention. Pluronic polyols, preferably Pluronic F68 or F88, and more preferably Pluronic F68 are protective agent/emulsifiers of the media of this invention which can act in conjunction with emulsifier(s) already present in the lipid/organic solvent solution making up the lipid component of the media of this invention as described below. However, the protective agent of the media of this invention need not be an emulsifier to be included within the definition herein of a protective agent.

If the protective agent is not also functioning as an emulsifier, the media of this invention further comprise another emulsifier that acts to emulsify the lipid component in conjunction with another emulsifier present at a small concentration in the lipid component itself as described below. Such an emulsifier alternative to a protective agent/emulsifier is preferably a detergent, preferably non-ionic which is non-toxic to the insect cell culture at the concentrations required for emulsification of the lipid component.

The introduction of the lipid component in the form of a microemulsion enhances the availability of lipids in the media to the cells. One option for emulsifying the lipid component is a dual emulsifier system wherein, as noted above, the protective agent is an emulsifier as well as a protective agent and can act in conjunction with an emulsifier or combination of emulsifiers present in the lipid/organic solvent solution making up the lipid component of the media of this invention. Another option for emulsifying the lipid component of the media of this invention is a system wherein the protective agent is not significantly emulsifying but wherein one or more additional emulsifiers are present in an aqueous solution which is added to the lipid component organic solution and act in conjunction with the emulsifiers present therein to form a microemulsion.

Testing whether an emulsifier, a protective agent/emulsifier, combination of emulsifiers, or a combination of a protective agent/emulsifier and an emulsifier or emulsifiers is effective in emulsifying the lipid component can be simply performed as follows. First, the candidate emulsifier or combination of emulsifiers must be confirmed as non-toxic to the insect cells of choice in a manner as described above. Secondly, the emulsifying ability of the candidate emulsifier(s) is tested at the determined non-toxic concentrations. The lipids are dissolved in an appropriate organic solvent, preferably an alcohol ($C_1$–$C_3$), more preferably ethanol. The candidate emulsifer or each of the combination of emulsifiers is then combined with the lipid/organic solution or in a separate aqueous solution, depending upon in which solution, that is, the organic or aqueous, the candidate emulsifier is more readily combinable. Then the aqueous solution is added to the lipid/organic solution and vigorously agitated as by vortexing. Upon agitation, a clear to slightly translucent microemulsion should form if the lipid component is successfully emulsified.

Preferred emulsifiers added to the lipid component of the media of this invention include phospholipids, preferably lecithin and non-toxic non-ionic polymeric detergents, preferably a polysorbate compound having the formula:

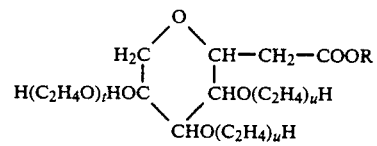

wherein R is a saturated or unsaturated fatty acid having from 16 to 20 carbons, inclusively;

wherein t is an integer between 10 and 30, inclusively; and wherein u is an integer between 10 and 20, inclusively.

Most preferably the non-toxic, non-ionic, polymeric detergent/emulsifier is polyoxyethylene (20) sorbitan monooleate, otherwise known as polysorbate 80. Such a non-toxic, non-ionic polymeric detergent is commercially available as Tween 80 from ICI Americas Inc. (New Murphy Road & Concord Pike, Wilmington, Del. 19897, U.S.A.). Another polysorbate 80 is commercially available as Durfax 80 from Durkee Industrial Foods Group/SCM Corp. (900 Union Commerce Bldg., Cleveland, Ohio 44115, U.S.A.). Other non-toxic, non-ionic, polymeric detergent candidate emulsifiers can be found in editions of McCutcheon's Emulsifiers and Detergents, supra.

Said non-ionic, non-toxic, polymeric detergent/emulsifier, such as, polysorbate 80, is present in the media of this invention at a concentration from about 5 mg/l to about 75 mg/l more preferably from about 20 mg/l to about 30 mg/l, and most preferably about 25 mg/l.

A preferred example of a dual emulsifier system of the media of this invention is the combination of a protective agent/emulsifier, preferably a Pluronic polyol, more preferably Pluronic F68 or Pluronic F88, and still more preferably Pluronic F68, and a non-toxic, nonionic polymeric detergent, preferably a polysorbate compound, and more preferably polysorbate 80.

In addition to an emulsifier or emulsifiers, the lipid component of the media of this invention comprise lipids essential for the growth of cells. Such lipids are preferably selected from the group comprising fatty acids, steroids and lipid soluble vitamins. Preferably, such fatty acids are fatty acid esters, more preferably polyunsaturated fatty acid esters, and still more preferably polyunsaturated fatty acid methyl esters. A preferred mixture of polyunsaturated fatty acid methyl esters for the media of this invention is fish liver oil, preferably cod liver oil which further contains vitamin A. Preferably, the steroids are sterols, and more preferably cholesterol. Preferably the lipid soluble vitamins comprise vitamin E (alpha-tocopherol) as well as vitamin A.

Further, the lipid component of the media of this invention comprise an organic solvent, preferably an alcohol, preferably containing from one to three carbons, and more preferably ethanol.

A mixture of polyunsaturated fatty acid methyl esters, such as, fish liver oil, preferably cod liver oil, is preferably present in the media at a concentration of from about 1 mg/l to about 50 mg/l, preferably from about 5 mg/l to about 15 mg/l and most preferably about 10 mg/l. Said concentrations of cod liver oil further contain the preferred concentrations of the lipid soluble vitamin A. The sterol, preferably cholesterol, is at a concentration from about 2 mg/l to about 7 mg/l more preferably from about 3 mg/l to about 5 mg/l, and most preferably about 4.5 mg/l. The alcohol, preferably ethanol, is at a concentration from about 0.5 ml/l to about 5 ml/l, more preferably about 1 ml/l. The alpha-tocopherol of the lipid component is at a concentration of from about 0.5 mg/l to about 4 mg/l, more preferably about 2 mg/l.

The lipid component is preferably added to the bulk of the media of the invention as a microemulsion. An advantage of the lipid component being in the form of a microemulsion, in addition to enhancing the availability of the lipids to the insect cells, is in providing the option of not having to filter sterilize the lipid component and the rest of the media components separately. The lipid component in the form of a microemulsion can be added to the media without being filter sterilized, and the entire media can then be filter sterilized without the concern that lipids, for example, in globular form, could be lost during the filter sterilization process. For large scale production, such an advantage is significant.

The lipid component of the media of this invention is prepared by combining the appropriate amount of the mixture of lipids, preferably a mixture of polyunsaturated fatty acids, alpha-tocopherol and cholesterol, and the emulsifier(s), in an appropriate amount of the organic solvent, preferably a $C_1$–$C_3$ alcohol to form a solution. At this point, an aqueous solution containing an emulsifier (or protective agent/emulsifier), which solution is approximately ten-fold greater in volume than the lipid component solution, optionally filter sterilized, can be slowly and, optionally aseptically, added to the lipid component solution with agitation as by vortexing. The lipid component microemulsion is thereby formed. It is the lipid microemulsion which is added to the media. As another option, the lipid component can then be easily filtered and sterilized, or the entire medium can be filter sterilized after all additions are completed.

An exemplary lipid component of the media of this invention comprises per liter of media:
10 mg cod liver oil
25 mg Tween 80
4.5 mg cholesterol
2 mg alpha-tocopherol
1 ml ethanol.

To the optionally filtered/sterilized lipid component solution (1 ml), then, in this exemplification, 10 ml of 10% Pluronic F68 in water (optionally filtered/sterilized) is slowly added with agitation as by vortexing.

The peptone component of the serum-free media of this invention can be selected from a wide variety of hydrolyzed protein products, either alone or in combination, including, without limitation, ox liver digest, such as Panmede (commercially available from Paines & Byrnes Ltd., Greenford, England), yeast extract, such as Yeastolate (preferably TC Yeastolate from Difco, U.S.A.), caseine digest, such as Bactocasitone (commercially available from Difco, U.S.A.), tryptose phosphate broth (TPB) wherein tryptose is the peptone, Lactalbumin Hydrolyzate (LH) (commercially available from Difco, U.S.A.) gelatin peptone, glycerin-gelatine peptone, and beef peptone among many other proteolytic digest products of proteins.

Preferably the peptone component is composed of peptone fractions either alone or in combination selected from the group comprising TPB, caseine digest preferably Bactocasitone, ox liver digest, preferably Panmede, yeast extract, preferably Yeastolate, and Lactalbumin Hydrolyzate (LH). More preferably, the peptone component comprises either LH or Yeastolate, alone or in combination. Still more preferably, the peptone component comprises either a combination of LH and Yeastolate or Yeastolate alone.

The total peptone concentration present in the media of this invention can be as high as the sum of the highest concentrations of the individual peptone fractions wherein said highest concentration for each peptone fraction is that which is non-toxic and noninhibitory to cell growth and wherein the total peptone concentration of said highest, non-toxic, noninhibitory concentrations of the peptone fractions is similarly non-toxic and noninhibitory to cell growth. The highest peptone concentrations can vary not only with the particular peptone fractions used but also with the particular insect cell line that is selected. In general, preferred total peptone concentration present in the media of this invention can range from about 1 g/l to about 12 g/l, more preferably from about 2 g/l to about 8 g/l, and still more preferably from about 3 g/l to about 5 g/l.

One example of a possible peptone component of the media of this invention employed for *Spodoptera frugiperda*, cell line Sf9, can be exemplified by a combination of TPB (from about 0 g/l to about 5 g/l, preferably about 2.5 g/l), Bactocasitone and Panmede wherein the latter two peptones are each at a concentration of about 0 g/l to about 5 g/l, preferably each at a concentration of about 1 g/l, a yeast extract, preferably Yeastolate at a concentration of from about 1 g/l to about 6 g/l, preferably from about 2 g/l to about 5 g/l, and LH at a concentration from about 0 g/l to about 6 g/l, preferably from about 1 g/l to about 4 g/l. Preferably, TPB is absent from said peptone component. More preferably, TPB, the caseine digest (Bactocasitone) and the ox liver digest (Panmede) are also absent from the peptone component, and the yeast extract, preferably Yeastolate alone at a concentration of from about 2 g/l to about 5 g/l, more preferably abut 4 g/l, or a combination of Yeastolate and LH, each at concentrations from about 0.5 g/l to about 4 g/l wherein the total peptone concentration is from about 3 g/l to about 5 g/l, preferably about 4 g/l, and more preferably where Yeastolate and LH are each at concentrations of about 2 g/l, are the peptone components.

Another preferred exemplary peptone component of the serum-free media of this invention comprises Yeastolate and LH, each at a concentration from about 0.5 g/l to about 6 g/l, preferably from about 1 g/l to about 4 g/l, and more preferably each at a concentration of about 2 g/l. As indicated above, the proportions of Yeastolate and LH are balanced such that the total peptone concentration of the media is within the stated range, and most preferably about 4 g/l.

Preferably, the peptones making up the peptone component of the serum-free media of this invention are prepurified by ultrafiltration to remove (1) any residual proteases used during the production of the peptone product; (2) any endotoxins; and (3) any high molecular weight components that could interfere with purification of any recombinant products expressed by the host insect cells once infected with a recombinant baculovirus or viral products produced by insect cells infected with wild-type viruses. Residual proteases could degrade recombinant proteins or viral products (for example by degrading the protein coat of viral particles) produced by the insect cells, and, therefore, ultrafiltration of the peptone fractions is considered a preferred mode of preparing the media of this invention. The peptone fraction(s) is (or are) first preferably prefiltered and then ultrafiltered through a membrane with a molecular weight cutoff selected to be smaller than the molecular weight of the recombinant or viral product to facilitate later purification, preferably a 2–15,000 molecular weight cutoff membrane, more preferably through a 2–10,000 molecular weight cutoff membrane, and still more preferably through a 10,000 molecular weight cutoff membrane such as a PM10 membrane (Amicon). Said ultrafiltration process is preferably carried out in a cross-flow filtration apparatus, for example, in a pressurized stirred cell for small scale or in a hollow fiber cartridge or plate and frame device for large-scale. The ultrafiltrate is then optionally filter sterilized before addition to the basal medium to which the other components of the media of this invention are also added.

A preferred peptone component of the serum-free media of this invention is prepared as follows:

A 10% stock solution of TC Yeastolate (Difco) is prefiltered through a 0.45 micron filter. The filtrate is then ultrafiltered through a 10,000 molecular weight cutoff membrane (Amicon PM10). The ultrafiltrate is then filter sterilized, and 20 ml thereof is added to 1 liter of the basal medium to which the lipid emulsion described above has already preferably been added. A 10% stock solution of LH is prefiltered, ultrafiltered, and then filter sterilized as directed for the Yeastolate fraction, and similarly 20 ml thereof is added to the medium.

The serum-free media of this invention can contain optional extra water soluble ingredients, such as, α-glycerol phosphate (at a concentration from about 0.25 g/l to about 4 g/l, preferably from about 0.5 g/l to about 2 g/l, and more preferably about 1 g/l), glycerol (at a concentration from about 0.5 g/l to about 5 g/l, preferably from about 1 g/l to about 3 g/l, and more preferably about 2 g/l), folic acid (at a concentration from about 1 mg/l to about 7 mg/l, preferably from about 2 mg/l to about 5 mg/l, and more preferably about 3.5 mg/l), and inositol (at a concentration from about 2 mg/l to about 20 mg/l, preferably about 5 mg/l to about 15 mg/l, and more preferably about 10 mg/l). Further, the optional extra water soluble ingredients can comprise anti-peroxidative enzymes, such as, catalase, at a concentration of from about 0.5 mg/l to about 10 mg/l, preferably from about 1 mg/l to about 5 mg/l, and more preferably about 3 mg/l.

However, as indicated in Example 6, below, the effect of eliminating such extra water soluble ingredients from the media of this invention was studied in an effort to simplify the medium and to remove any potential inhibitors of cell growth. Preliminary studies indicated that deletion of the most expensive of the extra water soluble ingredients, alpha-glycerol phosphate would be beneficial to cell growth. Further studies wherein all the extra water soluble ingredients were eliminated from the medium indicated that the length of the lag phase was reduced and the specific growth rate was increased. Therefore, the preferred serum-free media of this invention do not contain such extra water soluble ingredients.

Insect cells which can be grown successfully in the serum-free media of this invention and can produce viral products or recombinant proteins upon infection, respectively, with either wild-type viruses or recombinant baculoviruses, are those which have been shown to grow, reproduce and express recombinant and/or viral products in a medium containing serum. Thus, insect cells that can be grown in serum containing media can be grown in the media of this invention wherein the serum of the conventional media is replaced with the lipid component, peptone component, which is preferably ultrafiltered, and optionally, but preferably wherein the culture is to be well-aerated, with a protective agent as described herein.

Further, insect cells that can be grown in IPL-41 basal medium containing approximately 10% serum, can be grown in the serum-free media of this invention. For example, insect cell lines from *Bombyx mori*, *Lymantria dispar*, *Trichoplusia ni* and *Spodoptera frugiperda* are a few of the insect cells that have been grown successfully in basal media, such as IPL-41, containing approximately 10% serum. [See generally, Granados et al. (eds.), *The Biology of Baculoviruses* (CRC Press 1986); Vaughn, *Adv. Cell. Cult.*, 1:281 (1981); Vaughn, *J. Invert. Pathol.*, 28:233 (1976); Vaughn, In Maramorosch (ed.), *Invert. Tissue Culture: Research Applics.*, p. 295 (1976); and Vaughn, In, Barigozzi (eds.) *Proceedings of Internatl. Colloq. Invert. Tissue Culture*, (2nd, Tremezzo, 1967), p. 119 (1968).]

Further, such insect cells that can be grown in the media of this invention can be from any order of the Class Insecta which can be hosts to a baculovirus expression vector system, or other wild-type viruses, but are preferably from the Diptera or Lepidoptera orders. About 300 insect species have been reported to have nuclear polyhedrosis virus (NPV) diseases, the majority (243) of which were isolated from Lepidoptera. [Weiss et al., "Cell Culture Methods for Large-Scale Propagation of Baculoviruses," In Granados et al. (eds.), *The Biology of Baculoviruses:* Vol. II Practical Application for Insect Control, pp. 63–87 at p. 64 (1986).] Insect cell lines derived from the following insects are exemplary: *Carpocapsa pomonella* (preferably cell line CP-128); *Trichoplusia ni* (preferably cell line TN-368); *Autogra-*

*pha californica; Spodoptera frugiperda* (preferably cell line Sf9); *Lymantria dispar; Mamestra brassicae; Aedes albopictus; Orgyia pseudotsugata; Neodiprion sertifer; Aedes aegypti; Antheraea eucalypti; Gnorimoschema opercull-ela; Galleria mellonella; Spodoptera littolaris; Blatella germanica; Drosophila melanogaster; Heliothis zea; Spodoptera exigua; Rachiplusia ou; Plodia interpunctella; Amsaeta moorei; Agrotis c-nigrum, Adoxophyes orana, Agrotis segetum, Bombyx mori, Hyponomeuta malinellus, Colias eurytheme, Anticarsia germmetalia, Apanteles melanoscelus, Arctia caja*, and *Porthetria dispar*. Preferred insect cell lines are from *Spodoptera frugiperda*, and especially preferred is cell line Sf9. The Sf9 cell line used in the examples herein was obtained from Max D. Summers (Texas A & M University, College Station, Tex. 77843 U.S.A.). Other *S. frugiperda* cell lines, such as IPL-Sf-21AE III, are described in Vaughn et al., *In Vitro*, 13:213–217 (1977).

The insect cell lines of this invention are suitable for the reproduction of numerous insect-pathogenic viruses such as parvoviruses, pox viruses, baculoviruses and rhabdoviruses, of which nucleopolyhedrosis viruses (NPV) and granulosis viruses (GV) from the group of baculoviruses are preferred. Further preferred are NPV viruses such as those from Autographa spp., Spodoptera spp., Trichoplusia spp., Rachiplusia spp., Galleria spp. and Lymantria spp. More preferred are baculovirus strains *Autographa californica* NPV (AcNPV), *Rachiplusia ou* NPV, *Galleria mellonella* NPV and any plaque-purified strains of AcNPV, such as E2, R9, S1, M3, characterized and described by Smith et al., *J. Virol.*, 30:828–838 (1979); Smith et al., *J. Virol.*, 33:311–319 (1980); and Smith et al., *Virol.*, 89:517–527 (1978).

European patent application 127,839 (published Dec. 12, 1984) to Smith et al. describes a method for producing a recombinant baculovirus expression vector, capable of expressing a selected gene in a host insect cell. Said European application is herein incorporated by reference. The recombinant baculovirus expression vector is cotransfected with wild-type baculovirus DNA into a host insect cell, wherein recombination occurs. Recombinant baculoviruses are then detected and isolated according to methods described in EP 127,839 and Summers et al., "A Manual and Methods for Baculovirus Vectors and Insect Cell Culture Procedures" supra. The resultant recombinant baculovirus is then used to infect cultured insect cells and the protein product from the incorporated selected gene is expressed by the insect cells and secreted into the medium. Exemplified therein is the production of recombinant β-interferon, interleukin-2, and chloramphenicol acetyltransferase (CAT) via the culturing of *S. frugiperda* cells infected with a recombinant AcNPV expression vector into the genome of which the appropriate gene had been inserted. Further information concerning such a recombinant baculovirus expression system and its use in expressing recombinant proteins can be found in Summers et al., id.

Co-pending, commonly owned U.S. Ser. Nos. 07/077,188 entitled "Production of a Biologically Active Form or CSF-1 Using a Baculovirus (AcNPV)-Insect Cell Expression System", 07/077,586 entitled "Production of a Modified Plasminogen Activator Using a Baculovirus (AcNPV)-Insect Cell Expression System" and 07/077,126 entitled "Production of Ricin Toxin Proteins Using a Baculovirus (AcNPV)-Insect Cell Expression System" describe, respectively, the expression at high levels of biologically active recombinant colony stimulating factors, modified pro-urokinase, urokinase and novel hybrid proteins thereof, and ricin toxin proteins, wherein an insect cell/baculovirus expression system is employed to produce such proteins. Such applications have been filed concurrently with this application and are herein incorporated by reference.

U.S. Ser. No. 07/077,188 specifically describes the construction of baculovirus CSF-1 expression and transfer vectors, including pAcM4 and pAcM6, used to prepare the recombinant baculoviruses AcM4 and pAcM6 by cotransfection with baculovirus DNA in Sf9 cells. Said recombinant baculovirus transfer vectors pAcM4 and pAcM6 referred to in the examples below has been deposited at the American Type Culture Collection (ATCC) [12301 Parklawn Drive, Rockville, Md. 20852 (U.S.A.)] on June 12, 1987 in *E. coli*/MM294 under the respective designations ATCC Nos. 67429 and 67438. Said vectors have also been deposited and are maintained in the Cetus Master Culture Collection (CMCC) under the respective designations CMCC No. 3002 and CMCC No. 2996.

European Patent Application 127,839 and U.S. Ser. Nos. 07/077,188, 07/077,586 and 07/077,126, provide enablement concerning methods for producing recombinant baculovirus transfer vectors, and recombinant baculoviruses and for the use of the recombinant baculovirus expression system for expressing recombinant proteins in host insect cells.

According to the examples of this invention, recombinant CSF-1 is produced by the host insect cells cultured according to this invention. However, those skilled in the art who have the benefit of this disclosure, as well as the above applications incorporated by reference, will recognize that many other recombinant proteins can be produced by insect cells infected with recombinant baculovirus according to this invention. Other heterologous proteins that have been expressed in insect cells via the BEVS are outlined in Summers et al., *Banbury Report: Genetically Altered Viruses in the Environment,* 22:319–329 (1985). Exemplary recombinant proteins include, without limitation those described in copending, commonly owned applications (Cetus Docket Nos. 2347, 2382 and 2883) colony stimulating factors [for example, long and short form CSF-1 or M-CSF (described below), G-CSF, GM-CSF and interleukin-3 among others], modified pro-urokinase or urokinase, tissue plasminogen activator (TPA), TPA-urokinase hybrids, toxic proteins such as whole ricin toxin, ricin A chain, products containing ricin A, as well as, interferons ($\alpha$, $\beta$ and $\gamma$ and hybrids thereof), interleukins, tumor necrosis factor, erythropoietin and other hematopoietic growth factors, human growth hormone, as well as porcine, bovine and other growth hormones, epidermal growth factor, insulin, hepatitis B vaccine, superoxide dismutase, Factor VIII, Factor VIII C, atrial natriuretic factor, feline leukemia virus vaccines, as, for example, gp70 polypeptides, lectins such as *Ricin communis* agglutinin (RCA), diptheria toxin, gelonin, exotoxin from *Pseudomonas aeruginosa,* toxic proteins from *Phytolacca americana* (PAPI, PAPII and PAP-S), insecticidal proteins from *Bacillus thuringiensis,* many enzymes as for example, CAT, as well as innumerable other hybrid proteins.

"Colony stimulating factor (CSF-1)" refers to a protein which exhibits the spectrum of activity understood in the art for CSF-1, that is, when applied to the standard in vitro colony stimulating assay of Metcalf, *J. Cell Physiol.*, 76:89 (1970), it results in the formation of primarily macrophage colonies. Native CSF-1 is a glycosylated dimer; dimerization may be necessary for activity. The term CSF-1 herein refers to both dimeric and monomeric forms.

Human CSF-1 is operative both on human and murine bone marrow cells, whereas murine CSF-1 does not show activity with human cells. Therefore, human CSF-1 should be positive in the specific murine radioreceptor assay of Das et al., *Blood,* 58:630 (1981). The biological activity of the protein is also inhibited by neutralizing antiserum to human urinary CSF-1. Das et al., id.

CSF-1 is able to stimulate the secretion of series E prostaglandins, interleukin-1 and interferon from mature macrophages. Moore et al., *Science,* 223:178 (1984). However, the protein's ability to stimulate the formation of monocyte/macrophage colonies using bone marrow cells (bone marrow assay) and its susceptibility to inhibition by neutralizing antiserum against purified human urinary CSF-1 as well as a positive response to the radioreceptor assay (RRA) or a conventional radio-immunoassay (RIA) can be employed to identify CSF-1 produced by insect cells via a recombinant baculovirus expression vector system (BEVS).

As described in commonly owned, copending application U.S. Ser. No. 039,654, filed Apr. 16, 1987, the production of biologically active CSF-1 is complicated by the high degree of post-translational processing which includes glycosylation and dimerization. As indicated in commonly owned, co-pending U.S. Ser. No. 07/077,188, it is clear that the colony stimulating factors are secreted into the medium. Molecular weights of the CSF proteins produced indicate that the signal peptide is cleaved. The products also appear to be glycosylated.

Various forms of CSF-1, including a short form and a long form, have been described. See Kawasaki et al., *Science,* 230:291–296 (Oct. 18, 1985); Wong et al., *Science,* 235:1504–1508 (Mar. 20, 1987); U.S. Ser. No. 07/077,188, Clark et al., *Science,* 236:1229–1237 (June 5, 1987); and Metcalf, supra. Recombinant CSF-1, as well as muteins corresponding to the cDNA encoded forms are disclosed and claimed in co-pending, commonly owned U.S. Ser. Nos. 039,654 filed Apr. 16, 1987; 039,657 filed Apr. 15, 1987; 923,067 filed Oct. 24, 1986; and 876,819 filed June 20, 1986. Each of said applications are entitled "Recombinant Colony Stimulating Factor-1".

Recombinant baculovirus AcM4 carries a nucleotide sequence which encodes for a 150 amino acid form of rCSF-1 whereas the rbaculovirus AcM6 carries a nucleotide sequence which encodes for a 522 amino acid form of rCSF-1. Details concerning AcM4 and AcM6 used in the examples below can be found in U.S. Ser. No. 07/077,188.

The insect cells grown in the serum-free media of this invention are cultured in a temperature range and under conditions appropriate for the particular cell line selected. For example, *Spodoptera frugiperda* cells, preferably Sf9 cells, are cultured in a temperature range of from about 25° C. to about 32° C., preferably from about 27° C. to about 28° C. and wherein the pH of the culture medium is preferably maintained in a range of from about 6 to about 7, more preferably about 6.2 to about 6.4.

The effect of timing of the infection of the insect cells with a recombinant baculovirus has been shown to be critical for enhanced specific productivity. The specific production of the recombinant protein was found to be constant during the exponential phase of cell growth under non-oxygen limited conditions. Late infection, under non-exponential growth conditions, resulted in lower specific productivity and lower final titer. It is preferred that the exponential growth phase be extended to the highest possible cell densities to achieve the highest total productivity of the recombinant protein product. Infection of the host insect cells under conditions that limit growth, for example, in the stationary phase of cell growth, results in a reduced specific productivity of the recombinant protein product.

Specific productivity of the recombinant protein product is relatively independent of cell density at the time of infection as long as the culture is in exponential growth. For example, when *Spodoptera frugiperda* cells are the host insect cells and the media of this invention are used, preferred cell densities of from about $1.0 \times 10^6$ to about $4.0 \times 10^6$ cells/ml are preferred for infection with the recombinant baculovirus, more preferably from about 2.5 to about $3.5 \times 10^6$ cells/ml.

The timing of the harvest of the recombinant protein product is critical to avoid contamination of the recombinant protein by viral and cell lysis proteins and to simplify thereby the downstream purification of the recombinant product. With considerations for the stability of the product, it would be preferred to harvest the recombinant product before significant cell lysis has occurred. Further, each recombinant protein or viral product to be produced according to the methods and media of this invention should be checked for stability and degradation over the course of the fermentation run. Such considerations should enter into a determination of the optimal harvest time.

The following examples further illustrate the serum-free media of this invention, the growth of insect cells under non-oxygen limited conditions in such media and the production of recombinant protein products by such insect cells via a recombinant baculovirus expression vector system. These examples are not intended to limit the invention in any manner.

EXAMPLE 1

Development of a Serum-Free Growth Medium

This example outlines the development of a serum-free medium for the growth of insect cells. Results of growing *Spodoptera frugiperda* cells (Sf9) in a serum containing media, were compared with the growth of insect cells in two candidate serum-free media.

The control medium was IPL-41 complete medium as described in Weiss et al., *In Vitro,* 17(6):495–502 (June 1981) which is prepared by adding 2% (v/v) tryptose phosphate broth (TPB) and 10% (v/v) fetal bovine serum (FBS) to IPL-41 basal medium. Said complex control medium contains serum and protein hydrolysates at a total protein concentration of approximately 7 g/L.

Candidate serum-free medium #1 (SFM #1) was prepared by adding to IPL-41 basal medium, that is, IPL-41 complete medium wherein the TPB and FBS are omitted, the following supplements:

| | |
|---|---|
| Tryptose phosphate broth | 2.6 g/l |
| Bovine Serum Albumin (fatty acid free) | 1.0 g/l |
| Glycerol | 2.0 g/l |
| Pluronic Polyol (F68) | 1.0 g/l |

-continued

| | |
|---|---|
| Alpha-Glycerol Phosphate | 1.0 g/l |
| Folic Acid | 3.6 mg/l |
| Cod Liver Oil | 10.0 mg/l |
| Tween 80 | 25.0 mg/l |
| Cholesterol | 4.5 mg/l |
| α-tocopherol acetate | 2.0 mg/l. |

Candidate serum-free medium #2 (SFM #2) was similarly prepared by adding to IPL-"basal medium the following supplements:

| | |
|---|---|
| Tryptose Phosphate Broth | 2.6 g/l |
| Yeast Extract | 1.0 g/l |
| Bactocasitone | 1.0 g/l |
| Panmede | 1.0 g/l |
| Bovine Serum Albumin (fatty acid free) | 1.0 g/l |
| Glycerol | 2.0 g/l |
| Alpha-Glycerol Phosphate | 1.0 g/l |
| Pluronic polyol (F68) | 1.0 g/l |
| Inositol | 10.0 mg/l |
| Catalase | 3.0 mg/l |
| Folic Acid | 3.6 mg/l |
| Cod Liver Oil | 10.0 mg/l |
| Tween 80 | 25.0 mg/l |
| Cholesterol | 4.5 mg/l |
| α-Tocopherol acetate | 2.0 mg/l. |

The Sf9 cells in SFM #1 at passages 1, 2 and 3 grew at a rate and to a final cell density significantly reduced as compared to the cells in the serum-containing control media. Continued passage in the medium resulted in further decrease in growth.

The culture of Sf9 cells in SFM #2 at passage 1 went through a long lag phase followed by growth to densities typical for Sf9 cells grown in the 10% serum containing medium. At passage 2, the cells had adapted to the SFM #2 and did not demonstrate the long lag phase. The growth rate and final cell density again approximated those of cultures containing 10% FBS. SFM #2 was shown to support the growth of Sf9 cells for over seven passages.

EXAMPLE 2

Modified SFM #2 Supports Sf9 Growth and Expression of CSF-1

This example demonstrates that a modified version of SFM #2 of Example 1 supports both the growth of the *S. frugiperda* cells and their production of recombinant CSF-1 (short form) when the Sf9 cells are infected with a recombinant baculovirus AcM4 which has inserted within its genome a cDNA sequence encoding for a biologically active colony stimulating factor 1 (CSF-1) protein. Both the modified SFM #2 culture and 10% serum containing control culture of the Sf9 cells infected by the recombinant baculovirus produced approximately 300,000 U/ml of the recombinant CSF-1.

50 ml cultures of Sf9 cells were grown in 250 ml shake flasks agitated at 150 RPM with an orbital radius of gyration of onehalf inch at 27° C. Total cell counts were determined with a Coulter Counter and viability of the cells was checked by trypan blue exclusion. The cells were maintained in either IPL-41 complete medium as described above with 2% TPB and 10% heat inactivated FBS plus 0.1% Pluronic polyol (F68) or in modified SFM #2 (SFM2M) as described immediately below.

The SFM #2 of Example 1 contains 1 g/l of bovine serum albumin (BSA). The other major substitute therein for serum is a combination of three peptones, each supplied at 1 g/l as follows: yeast extract, Bactocasitone and Panmede. Modification of the peptone content of SFM #2 was investigated to simplify downstream purification of the recombinant protein product. In addition to the 3 g/l of peptones, the SFM #2 further contains 2.6 g/l tryptose phosphate broth (2 g/l tryptose as does the IPL-41 complete medium). It was found by reducing the peptone concentration to 1.5 g/l, 0.6 g/l, 0.3 g/l and to 0 g/l respectively, whereas the TPB concentration was maintained at 2.6 g/l and by comparing the growth curves to those of cultures grown at 3 g/l of peptones, that the peptone concentration was critical. The 3 g/l peptone culture of SFM #2 resulted in a satisfactory cell growth rate, that is, a population doubling time (Td) of 24 hours as compared to 17 hours for a typical 10% serum containing culture, and maximum cell densities of $4-5 \times 10^6$ cells/ml which were equivalent to 10% serum containing cultures. However, when the peptone concentration was reduced from 3 g/l to 0 g/l the maximum cell density attained was significantly reduced.

The peptones were ultrafiltered to remove (1) any high molecular weight components that might interfere with product purification; (2) potentially residual proteases from the peptone production process; and (3) endotoxins. The peptones, but not the TPB, were ultrafiltered with a pressurized stirred cell through a 10,000 molecular weight cut-off membrane (Amicon PM10) before being added to the serum-free medium. Growth of the Sf9 cells on the serum-free medium containing the peptone filtrate was found to be equivalent to that with the whole peptone. The peptone ultrafiltrate retentate was diafiltered 20× with water; it was shown not to enhance growth of the Sf9 cells significantly as compared to serum-free culture wherein no additional peptone was added.

It was determined that the TPB presented problems in the purification of the recombinant CSF-1. Therefore, TPB was ultrafiltered as described above for the three peptones through a PM10 membrane prior to addition to the serum-free medium. The combination of the PM10 filtrates of both the TPB and three peptones resulted in growth of Sf9 to a maximum cell density similar to the 10% serum containing media and to the unfiltered SFM #2.

Thus, a new serum-free medium version designated SFM2M contains all peptones including TPB pre-ultrafiltered. Growth in the 10% serum medium was faster than in SFM2M.

The cultures were directly infected with the recombinant baculovirus AcM4. The construction of the transfer vector pAcM4 (containing the short clone CSF-1) is described in co-pending, commonly owned U.S. Ser. No. 07/077,188. The methods of preparing recombinant baculovirus AcM4 by cotransfecting insect cells with pAcM4 and wild-type baculovirus DNA and then detecting and purifying the recombinant baculovirus were carried out essentially as described in said U.S. patent application. [See also, European Patent Application No. 127,839 and Summers et al., "A Manual of Methods for Baculovirus Vectors and Insect Cell Culture Procedures", supra.]

Infection with the recombinant baculovirus was performed at relatively low cell density ($1-1.5 \times 10^6$ cells/ml) with a multiplicity of infection (MOI) of 2. Both the SFM2M and 10% serum containing control culture produced 300,000 U/ml of the recombinant CSF-1. The CSF-1 levels were estimated by RIA.

Most of the CSF-1 was produced within 48 hours after infection with the recombinant baculovirus, and before the cells had lysed. To avoid contamination of the culture supernatant by cell lysis, it is desirable to time the harvest of the recombinant protein product harvest prior to cell lysis.

It was determined that $10^6$ U of recombinant CSF-1/ml could be produced by Sf9 cells infected with the recombinant baculovirus AcM4 in SFM2M during the exponential growth phase. The specific production (U/cell) of the recombinant CSF-1 appeared to be constant during the exponential phase of growth, under non-oxygen limited conditions. Infection with AcM4 at a cell density of $2.7 \times 10^6$ cells/ml produced $1.2 \times 10^6$ U of rCSF-1/ml by RIA and $2.5 \times 10^6$ U rCSF-1/ml as estimated by the bone marrow bioassay. [The bone marrow proliferation assays are performed according to Moore et al., *J. Immunol.*, 131:2374 (1983) and Prystowsky et al., *Am. J. Pathol.*, 114:149 (1984).] Little change was noted in the (short clone) rCSF-1 by Western analysis of samples from day 1 through day 4 postinfection. Late infection, under non-exponential growth conditions, resulted in a lower specific productivity and lower final titer. It was therefore concluded that infection at higher cell density (but still in the exponential growth phase) would increase rCSF-1 production.

EXAMPLE 3

Elimination of BSA from SFM2M

This example shows that the growth of Sf9 cells in SFM2M containing 1 g/l of bovine serum albumin (BSA) was similar to that found in SFM2M without any BSA. Likewise, the production of rCSF-1 in such an essentially protein-free medium (SFM2M without BSA) was equivalent to that seen in SFM2M with BSA.

50 ml cultures of Sf9 cells were grown in 250 ml shake flasks agitated at 100-150 rpm (with an orbital radius of one-half inch) at 27° C., in both SFM2M and SFM2M without BSA. The recombinant baculovirus AcM4 was used to infect exponentially growing cultures at a MOI of 1. Little or no effect on growth rate or maximum cell density was observed in the cultures without BSA versus those with BSA.

A number of other SFM2M with no BSA cultures of Sf9 cells have been grown in shake flasks and infected with AcM4. Culture volumes of 25-250 ml in 125-1,000 ml flasks have repeatedly produced $10^6$ U rCSF-1/ml, by 4 or 5 days after infection.

Immunoprecipitation, followed by SDS-PAGE, as well as Western analysis, indicated that the rCSF-1 (short clone) is not degraded in the culture broth of this essentially protein-free medium, that is, SFM2M with no BSA.

The SFM2M with no BSA still contains 3 mg/l catalase and 5 g/l mixed peptones of molecular weight lower than 10,000. The composition of SFM2M with no BSA is as follows:

| IPL-41 Basal Medium | |
|---|---|
| Ultrafiltered Peptones | |
| Tryptose Phosphate Broth | 2.6 g/l |
| Bactocasitone (caseine digest) | 1 g/l |
| Panmede (ox liver digest) | 1 g/l |
| Yeastolate (yeast extract) | 1 g/l |
| Extra Water Soluble Ingredients | |

| -continued | |
|---|---|
| IPL-41 Basal Medium | |
| α-Glycerol phosphate | 1 g/l |
| Glycerol | 2 g/l |
| Folic Acid | 3.6 mg/l |
| Inositol | 10 mg/l |
| Catalase | 3 mg/l |
| Pluronic polyol-lipid Emulsion | |
| Pluronic polyol F68 | 1 g/l |
| Cod Liver Oil | 10 mg/l |
| Tween 80 | 25 mg/l |
| Cholesterol | 4.5 mg/l |
| α-Tocopherol acetate | 2 mg/l |

EXAMPLE 4

Importance of Physical Protectant

It was found that although BSA is not necessary for Sf9 cell growth or production of the recombinant protein product that the elimination of the Pluronic polyol (F68) from the medium even in the presence of 10% serum results in cell death in shake flask cultures. The Pluronic polyol is essential as a physical protectant in shake flasks, and it also serves to emulsify lipids.

EXAMPLE 5

Peptone Modifications of SFM2M without BSA

Example 3 outlines the composition of SFM2M without BSA. In this example, more simplified media are described wherein the peptone component of SFM2M without BSA is modified.

The total peptone composition of SFM2M without BSA is 5 g/l. The growth rate of Sf9 cells in such medium was slow with a doubling time (Td) of 30-45 hours after numerous passages (10-20), whereas the doubling time (Td) of Sf9 cells in 10% serum containing medium is from about 17-24 hours. The peptone composition of SFM2M without BSA was modified to obtain a faster growth rate and thereby more efficient production of recombinant proteins from Sf9 cells infected with a recombinant baculovirus. Also, a reduction in the number of peptones simplifies media preparation and downstream purification of the recombinant protein product.

Peptone modifications of SFM2M without BSA were prepared wherein, to media containing TPB at 2.6 g/l, the following peptone additions were made:

(1) 3 g/l Yeastolate, or
(2) 3 g/l Bactocasitone, or
(3) 3 g/l Panmede.

Further, two media were prepared wherein tryptose (as TPB) was the only peptone component at 2 g/l and 5 g/l, respectively. The media were inoculated with Sf9 cells that had been maintained in SFM2M without BSA for over 15 passages (about 50+ generations). The Sf9 cultures of 50-100 ml in 250 ml shake flasks were agitated at 100-150 rpm at 27° C. Cell density was measured with a Coulter Counter. Typical cell viabilities of exponential phase cultures has been 99-100% as determined by trypan blue exclusion.

The poorest growth was found in the medium containing only TPB (at both 2 and 5 g/l tryptose), as the peptone component. The addition of the other peptones to the medium enhanced growth significantly. The best growth was found in the medium containing TPB plus Yeastolate, although a long lag phase (two to three days before exponential growth began) was noted.

As the TPB appeared to inhibit cell growth, peptone modifications of SFM2M without BSA media were prepared wherein TPB was eliminated. Panmede at 5 g/l as the only peptone component of modified SFM2M without BSA appeared to inhibit growth. Bactocasitone at 5 g/l as the only peptone component supported growth to a low cell density and at a slow exponential growth. The tripeptone (Yeastolate, Panmede and Bactocasitone) at 5 g/l and Yeastolate only at 5 g/l cultures both grew well; however, the Yeastolate culture, again, had the fastest exponential growth rate, but a long lag phase.

Experiments with Yeastolate alone as the peptone component at 2, 4, 6, 8 and 10 g/l, respectively, indicated that at concentrations of 4 g/l and above, increasingly longer lag phases or inhibition of exponential growth occurred. There was a short lag phase in cultures containing Yeastolate at 2 g/l. Although the 4 g/l Yeastolate culture had a long lag phase, it grew the fastest and achieved slightly higher maximum cell densities.

To reduce the lag phase of such cultures containing Yeastolate as the peptone component of the media, Yeastolate at a low concentration (2 g/l) was combined with ultrafiltered Lactalbumin Hydrolyzate (LH) at 0, 2 and 4 g/l respectively, because LH had been shown by preliminary studies to support a fast growth rate with no lag phase. The LH apparently reduced the lag phase of the 2 g/l Yeastolate culture and increased the maximum cell density. However, a 4 g/l Yeastolate culture without LH demonstrated a relatively short lag phase indicating that the Sf9 cells having been grown for several passages in the 4 g/l Yeastolate medium apparently adapted to its inhibitory effects.

This example thus indicates that the peptone composition of SFM2M without BSA could be advantageously modified to contain Yeastolate alone at 4 g/l or Yeastolate plus LH (2 g/l each) as the peptone component.

EXAMPLE 6

Elimination of Water Soluble Ingredients: ISFM-3 and ISFM-4

In parallel with the peptone modification studies described in Example 5, the role of other ingredients of SFM2M without BSA were examined. As shown in Example 3, SFM2M without BSA contains the following defined water soluble ingredients: α-glycerol phosphate (1 g/l); glycerol (2 g/l); folic acid (3.6 g/l); inositol (10 mg/l); and catalase (3 mg/l). The first four such ingredients had been added to the serum-free media because of growth stimulatory effects claimed in the literature for another Lepidopteran insect cell line. [Goodwin et al., *Invertebrate Systems* (1980), supra.] Catalase had been added as a protectant from peroxidation damage that was anticipated to occur under the highly aerated conditions used to grow Sf9 cells in shake flasks.

It was found that removal of these water soluble ingredients from the SFM2M medium without BSA had beneficial effects on cell growth, reducing the lag phase and increasing the specific growth rate, while maintaining the maximum cell density. Thus, the serum-free medium was simplified to contain: (1) basal medium (IPL-41); (2) Pluronic polyol-lipid emulsion; and (3) peptone(s) of choice.

SFM2M without BSA and without the water soluble ingredients wherein the peptone component comprises 2 g/l Yeastolate and 2 g/l LH was designated ISFM-3, and wherein the peptone component comprises 4 g/l Yeastolate, such medium was designated ISFM-4. Both the ISFM-3 and ISFM-4 cultures grew well but the ISFM-4 culture was shown to have a longer lag phase. The compositions of ISFM-3 and ISFM-4 therefore are as follows:

| IPL-41 Basal Medium | |
| --- | --- |
| Ultrafiltered Peptones | 4 g/l |
| Pluronic Polyol-Lipid Emulsion | |
| Pluronic Polyol F68 | 1 g/l |
| Cod Liver Oil | 10 mg/l |
| Tween 80 | 25 mg/l |
| Cholesterol | 4.5 mg/l |
| α-Tocopherol Acetate | 2 mg/l | wherein the ultrafiltered peptones comprise 2 g/l of Lactalbumin Hydrolysate (LH) and 2 g/l of Yeastolate for ISFM-3; and wherein the ultrafiltered peptones comprise 4 g/l of Yeastolate for ISFM-4. In addition, both the ISFM-3 and ISFM-4 media contain 1 ml/l of ethanol.

To overcome the problem of the ISFM-4 lag phase, a Yeastolate fed-batch culture was tested. An ISFM medium containing 2 g/l Yeastolate (no other peptones and no extra water soluble ingredients) was used to grow Sf9 cells to $1.2 \times 10^6$ cells/ml. At that point, an additional 1 g/l of Yeastolate was added to the culture. The culture was then grown to $2.6 \times 10^6$ cells/ml, and an additional 2 g/l of Yeastolate was added. The strategy resulted in a reduced lag phase (15 hours), rapid cell growth (equivalent to 10% serum containing cultures) and increased maximum cell densities in cultures fed with higher amounts of Yeastolate (up to $6-7 \times 10^6$ cells/ml).

The long lag phase of ISFM-4 culture without the Yeastolate fed batch approach further became less of a problem upon continued passaging of Sf9 in the medium, probably because of adaptation to the Yeastolate. Cultures grew equally well with short lag phases in ISFM-3 and ISFM-4 by the third passage. Table 2 lists the average growth characteristics of 8 passages in these two media. These media provide growth rates (Td = 17-24 hours) and maximum cell densities ($5 \times 10^6$ cells/ml) similar to those found in 10% serum media.

TABLE 2

| | Lag Phase* (hours) | Population Doubling Time (hours) | Maximum Cell Density ($10^6$ cells/ml) |
| --- | --- | --- | --- |
| ISFM-3 | 14 | 22 | 5.0 |
| ISFM-4 | 15 | 22 | 6.1 |

*Lag phase was calculated by extrapolating the exponential phase plot (semi-log) back to the initial cell density ($1 \times 10^5$ cells/ml). The x-intercept (hours of culture incubation) is equal to the lag phase.

EXAMPLE 7

Production of Recombinant CSF-1 by Insect Cells Grown in Serum-Free Media and Infected with Recombinant Baculovirus AcM4

Sf9 cells grown for 25-30 passages (75-120 generations) in the serum-free media of this invention were tested for production of rCSF-1 upon infection with the recombinant baculovirus AcM4. Table 3 lists such Sf9 cultures infected with AcM4 under similar exponential growth conditions. Such cultures were grown according to the procedures outlined in the above examples.

TABLE 3 rCSF-1 Production by Sf9 Cells Growing in Various Media at 5 Days after Infection with AcM4

| Media | Cell Density at Infection ($10^6$ cells/ml) | rCSF-1 Produced by Five Days Postinfection ($10^5$ RIA U/ml) |
|---|---|---|
| 10% Serum* | 3.2 | 9.1 |
| SFM2M without BSA | 2.5 | 10.2 |
| ISFM-3 | 3.1 | 10.1 |
| ISFM-4 | 3.0 | 9.9 |

*10% serum is IPL-41 complete medium with TPB and FBS.

As shown in Table 3, all of the cultures produced similar levels of rCSF-1, at about $10^6$ U/ml as estimated by RIA. The production of rCSF-1 was not affected by the slower exponential growth rate afforded by the SFM2M without BSA medium.

EXAMPLE 8

Sf9 Adaptation to SFM2M without BSA, ISFM-3 and ISFM-4

It was found that the original Sf9 maintained in the 10% serum containing medium (IPL-41 complete medium) readily adapted to SFM2M without BSA, ISFM-3 and ISFM-4 upon the first and second passages. Subsequent passages and infections with the recombinant baculovirus AcM4 have verified the results described above and indicate that SFM2M without BSA, ISFM-3 and ISFM-4 are a suitable media for large-scale growth of insect cells and for the production of recombinant protein products thereby via a recombinant baculovirus expression vector system.

EXAMPLE 9

Production of Recombinant CSF-1 by Insect Cells Grown in ISFM-4 and Infected with Recombinant Baculovirus AcM6

50 ml cultures of Sf9 insect cells were grown in 250 ml shake flasks agitated at 100–150 rpm (with an orbital radius of one-half inch) at 27° C., in ISFM-4. The recombinant baculovirus AcM6 was used to infect an exponentially growing culture at an MOI (multiplicity of infection) of 1.

To determine the optional time to harvest the rCSF-1, samples of the culture were removed daily after infection with the recombinant baculovirus, centrifuged and supernatants immediately frozen. These samples were analyzed for rCSF-1 using Western blotting, RIA and bone marrow assay. Samples containing 600 RIA units of rCSF-1, that had been diafiltered into 0.1 M $NaPO_4$ (pH 6.8) and reduced with $\beta$-mercaptoethanol, were run on SDS-PAGE for Western analysis. Rabbit antiserum to denatured, monomeric 18K-A rCSF-1 (158 amino acids) from E. coli were used as the primary antibodies for detection of rCSF-1. The blots were developed using goat anti-rabbit IgG followed by iodination with $^{125}$I-protein A to visualize the proteins through autoradiography.

Figure 1C:
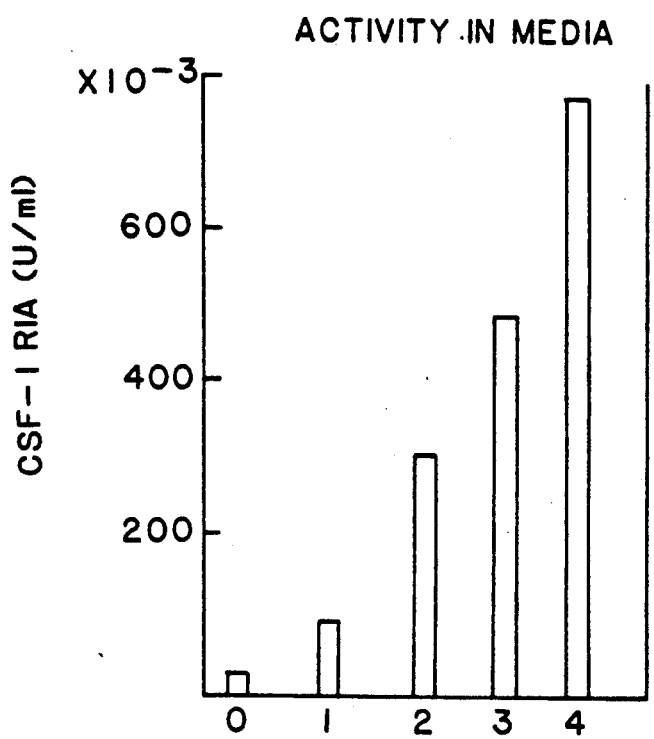

FIG. 1 shows the time course of: rCSF-1 concentration in culture medium (top panel), insect cell viability (middle panel) and Western analysis of rCSF-1 homogeneity. On the day of infection with the rbaculovirus, only trace levels of secreted rCSF-1 were present by RIA (top panel, day 0). rCSF-1 concentration (by RIA) increased through day 4 and reached a peak of $8 \times 10^5$ U/ml Bone marrow assays confirmed the RIA data.

Western blot analysis (lower panel) of 600 RIA units from each of the daily samples of the culture supernatant shows that rCSF-1 consisted of a triplet band of about 40K and a single band of 70K on days 1 through 3 post-infection. The relative intensity of the 70K band decreased on day 3. On day 4, a new set of 4 rCSF-1 bands appeared, of apparent sizes 45K, 35K, 25K and 20K. This major change in rCSF-1 by day 4 was correlated with the rapid death phase of the infection/production process (top panel). Although the biological activity of the rCSF-1 was retained (as confirmed by the bone marrow assay), the sizes and heterogeneity of the protein were changed. This suggests that the timing of harvest of this AcM4 rCSF-1 can be optimized to obtain the most preferred rCSF-1 product.

In contrast to the lability of the rCSF-1 produced by infections of the insect cells by AcM6, the rCSF-1 produced by insect cells infected with AcM4 according to Example 7, above, did not change significantly in size or heterogeneity through the cell death phase, and up to 5 days after infection.

Conclusion

In summary, it can be seen that the serum-free media of this invention provide simplified, low-cost media for the large-scale growth of insect cells under agitated and/or sparged, preferably well-aerated conditions, and for the production therefrom of recombinant proteins via a recombinant wild-type baculovirus expression vector system or other viral products by infection with viruses. Such media simplify the purification of the recombinant protein and viral products by their low or essentially no protein content, lack of serum, and by ultrafiltration of the peptone components thereof.

Deposit

As mentioned above, the recombinant baculovirus transfer vectors pAcM4 and pAcM6 in E. coli/MM294 have been deposited at the American Type Culture Collection (ATCC), 12001 Parklawn Drive, Rockville, Md. 20852 (U.S.A.) on June 12, 1987 under the respective ATCC Nos. 67429 and 67428.

Said deposits were made pursuant to a contract between the ATCC and the assignee of this patent application, Cetus Corporation. The contract with the ATCC provides for permanent availability of said strains and progeny thereof to the public upon issuance of a U.S. patent related to this application describing and identifying the deposits or upon the publication or laying open to the public of any U.S. or foreign patent application, whichever comes first, and for the availability of the strains and the progeny thereof to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the strains on deposit should die or be lost or destroyed when cultivated under suitable conditions, they will be promptly replaced upon notification with a viable culture of the same strain.

The deposits under the terms of the Budapest Treaty assure that said cultures deposited will be maintained in a viable and uncontaminated condition for a period of at least five years after the most recent request for the furnishing of a sample of the deposited microorganism was received by the ATCC and, in any case, for a period of at least 30 years after the date of the deposit.

Availability of the deposited strains is not to be construed as a license to practice the invention in contravention of the rights granted under the authority of any government in accordance with its patent laws.

Also, the present invention is not to be considered limited in scope by the deposited recombinant transfer vectors, since the deposited vectors are intended only to be illustrative of particular aspects of the invention. Any recombinant baculovirus transfer vector which can be used to prepare recombinant baculoviruses which can function to infect a host insect cell to produce a recombinant protein product is considered to be within the scope of this invention. Further, various modifications of the invention in addition to those shown and described herein apparent to those skilled in the art from the preceding description are considered to fall within the scope of the appended claims.

We claim:

1. A serum free medium which supports the large scale growth of insect cells, excluding monolayer culture, and the production thereby of recombinant and viral products at levels comparable to those achieved in serum containing media, the serum free medium comprises:
  (a) a basal medium;
  (b) a lipid component;
  (c) a peptone component; and
  (d) a protective agent;
wherein:
  the lipid component is in the form of a microemulsion;
  the basal medium comprises a nutrient mixture of inorganic salts, sugars, amino acids, optionally also containing vitamins, organic acids and/or buffers;
  the protective agent comprises an emulsifying, non-toxic, water soluble compound that protects the insect cells from damage and death under well-aerated culture conditions, wherein the protective agent is selected from the group consisting of hydroxyethyl starch, methyl cellulose, carboxymethyl cellulose, dextran sulfate, polyvinylpyrrolidone, ficoll, alginic acid, polypropyleneglycol and non-toxic polymeric detergents;
  the lipid component further comprises an emulsifier, an organic solvent, and lipids essential for the growth of insect cells;
  the emulsifier of the lipid component comprises a phospholipid and/or a non-toxic, nonionic polymeric detergent;
  the organic solvent comprises an alcohol containing from one to three carbon atoms;
  the lipids of the lipid component are selected from the group consisting of fatty acids, steroids and lipid soluble vitamins; and
  the peptone component comprises a hydrolyzed protein product or a mixture of hydrolyzed protein products, the peptone component is at a total concentration of from about 1 g/l to about 12 g/l.

2. A serum free medium according to claim 1 wherein the protective agent comprises a non-toxic, non-ionic polymeric detergent;
  the emulsifier of the lipid component comprises lecithin and/or a polysorbate compound wherein said polysorbate comprises the formula;

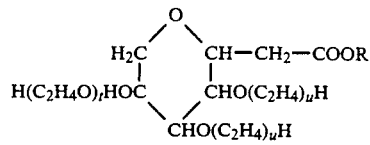

wherein R is a saturated or unsaturated fatty acid having from 16 to 20 carbons, inclusively;
  wherein t is an integer between 10 and 30, inclusively;
  u is an integer between 10 and 20, inclusively;
  the organic solvent is ethanol;
  the lipids of the lipid component are selected from the group consisting of fatty acid esters, sterols, Vitamin A and alpha-tocopherol; and
  peptones of the peptone component are selected from the group consisting of caseine digest, ox liver digest, yeast extract, tryptose phosphate broth (TPB) and Lactalbumin Hydrolyzate (LH).

3. A serum free medium according to claim 2 wherein the non-toxic, non-ionic polymeric detergent comprises a block copolymer of propylene oxide and ethylene oxide;
  the lipids of the lipid components are selected from the group consisting of polyunsaturated fatty acid esters, sterols, Vitamin A and alpha-tocopherol; and
  the peptones of the peptone component are selected from the group consisting of ox liver digest, TPB, yeast extract, caseine digest, and Lactalbumin Hydrolyzate (LH).

4. A serum free medium according to claim 3 wherein the non-toxic, nonionic polymeric detergent is a Pluronic polyol;
  the emulsifier of the lipid component comprises lecithin and/or polysorbate 80;
  the lipids of the lipid component are selected from the group consisting of polyunsaturated fatty acid methyl esters, sterols, Vitamin A and alpha-tocopheral; and
  the peptones of the peptone component are selected from the group consisting of TPB at a concentration from about 0 g/l to about 5 g/l, caseine digest and ox liver digest wherein the latter two peptones are each at a concentration of about 0 g/l to about 5 g/l, and yeast extract at a concentration of from about 1 g/l to about 6 g/l, and LH at a concentration from about 0 g/l to about 6 g/l.

5. A serum free medium according to claims 4 wherein the basal medium is IPL-41;
  the Pluronic polyol is selected from the group consisting of Pluronic F68, F88 and F108;
  the lipids of the lipid component are selected from the group consisting of fish liver oil, cholesterol and alpha-tocopherol; and
  the peptones of the peptone component are selected from the group consisting of yeast extract and LH.

6. A serum free medium according to claim 5 wherein the Pluronic polyol is selected from the group consisting of Pluronic F68 and Pluronic $F_{88}$;
  the lipids of the lipid component are selected from the group consisting of cod liver oil and cholesterol; and
  the peptones of the peptone component are selected from the group consisting of Yeastolate and LH.

7. A serum free medium according to claim 6 wherein the lipid component comprises cod liver oil at a concentration from about 1 mg/l to about 50 mg/l cholesterol at a concentration from about 2 mg/l to about 7 mg/l ethanol at a concentration from about 0.5 ml/l to about 5 ml/l, polysorbate 80 concentration from about 20 mg/l to about 30 mg/l and the alphatocopherol at a concentration of from about 0.5 mg/l to about 4 mg/l; and peptone component is at a total concentration of about 3 g/l to about 5 g/l.

8. A serum free medium according to claim 6 wherein the Pluronic polyol is Pluronic F68 at a concentration of from about 0.05% to about 0.5%; and the lipid component comprises cod liver oil at a concentration from about 5 mg/l to about 15 mg/l, cholesterol at a concentration from about 3 mg/l to about 5 mg/l, ethanol at a concentration of about 1 ml/l, polysorbate 80 at a concentration of about 25 mg/l and alpha-tocopherol at a concentration of about 2 mg/l.

9. A serum free medium according to claim 8 wherein the Pluronic F68 is at a concentration of about 0.1%; the cod liver oil is at a concentration of about 10 mg/l;

the cholesterol is at a concentration of about 4.5 mg/l; and the peptone component comprises Yeastolate at a concentration of about 2 g/l to about 5 g/l and LH at a concentration from about 1 g/l to about 4 g/l.

10. A serum free medium according to claim 9 wherein the peptone component is ultrafiltered and comprises a combination of Yeastolate and Lactalbumin Hydrolyzate wherein each is at a concentration from about 0.5 g/l to about 4 g/l.

11. A serum free medium according to claim 10 wherein the peptone component comprises Yeastolate at about 2 g/l and Lactalbumin Hydrolyzate at about 2 g/l.

12. A serum free medium according to claim 9 wherein the peptone component comprises Yeastolate at a concentration of about 4 g/l.

13. A serum-free medium according to claim 11 designated ISFM-3.

14. A serum-free medium according to claim 12 designated ISFM-4.

* * * * *